US011618875B2

(12) United States Patent
Papermaster et al.

(10) Patent No.: US 11,618,875 B2
(45) Date of Patent: Apr. 4, 2023

(54) DATA COLLECTION AND ANALYTICS BASED ON DETECTION OF BIOLOGICAL CELLS OR BIOLOGICAL SUBSTANCES

(71) Applicant: Nano Global, Austin, TX (US)

(72) Inventors: Steven Papermaster, Austin, TX (US); Zoltan Papp, Austin, TX (US); Christine Scheve, Austin, TX (US); Aaron Papermaster, Austin, TX (US); Eric Crawford, Austin, TX (US)

(73) Assignee: Nano Global Corporation, Austin, TX (US)

( * ) Notice: Subject to any disclaimer, the term of this patent is extended or adjusted under 35 U.S.C. 154(b) by 315 days.

(21) Appl. No.: 16/765,324

(22) PCT Filed: Nov. 19, 2018

(86) PCT No.: PCT/US2018/061841
§ 371 (c)(1),
(2) Date: May 19, 2020

(87) PCT Pub. No.: WO2019/100012
PCT Pub. Date: May 23, 2019

(65) Prior Publication Data

US 2020/0354667 A1 Nov. 12, 2020

Related U.S. Application Data

(60) Provisional application No. 62/588,754, filed on Nov. 20, 2017, provisional application No. 62/644,331, filed on Mar. 16, 2018.

(30) Foreign Application Priority Data

Aug. 22, 2018 (WO) ................ PCT/US2018/047568

(51) Int. Cl.
*G16H 30/40* (2018.01)
*C12M 1/34* (2006.01)
(Continued)

(52) U.S. Cl.
CPC ............ *C12M 41/36* (2013.01); *G16B 45/00* (2019.02); *G16B 50/00* (2019.02); *G16H 30/40* (2018.01); *G16H 40/63* (2018.01); *G16H 50/30* (2018.01)

(58) Field of Classification Search
CPC ........... G06N 3/00; G06N 3/02; G06V 20/69; G06V 20/693; G06V 20/698;
(Continued)

(56) References Cited

U.S. PATENT DOCUMENTS

2005/0207633 A1 9/2005 Arini et al.
2011/0058728 A1 3/2011 Perner
(Continued)

FOREIGN PATENT DOCUMENTS

EP 2985719 A1 2/2016
WO 2010022391 A2 2/2010
WO 2016161022 A2 10/2016

OTHER PUBLICATIONS

Supplementary European Search Report for EP Application No. 18878535.6 (PCT/US2018/061841) dated Nov. 18, 2021.
(Continued)

*Primary Examiner* — Antonio A Caschera
(74) *Attorney, Agent, or Firm* — Terrile, Cannatti & Chambers, LLP; Emmanuel A. Rivera

(57) ABSTRACT

Techniques related to the detection or identification of biological cells or substances.

18 Claims, 5 Drawing Sheets

500

510 OBTAIN IMAGE-BASED DATA OF IMAGE OF SCENE THAT INCLUDES BIOLOGICAL CELLS OR SUBSTANCES

520 DETECT BIOLOGICAL CELLS AND/OR SUBSTANCES

530 OBTAIN ENVIRONMENTAL FACTORS

540 REPORT RESULTS

550 CORRELATION; INFERENCE; RANKING; AND/OR AMELIORATION

(51) Int. Cl.

| | |
|---|---|
| ***G16H 50/30*** | (2018.01) |
| ***G16H 40/63*** | (2018.01) |
| ***G16B 45/00*** | (2019.01) |
| ***G16B 50/00*** | (2019.01) |

(58) Field of Classification Search

CPC ......... G06T 7/0012; G06T 2007/30004; G06T 2007/30072; G06T 2007/30024; G09G 2380/08; C12M 41/36; G16H 50/30; G16H 30/40; G16H 40/63; G16B 45/00; G16B 50/00

See application file for complete search history.

(56) References Cited

U.S. PATENT DOCUMENTS

| | | | |
|---|---|---|---|
| 2013/0038727 | A1 | 2/2013 | Clark |
| 2013/0273524 | A1 | 10/2013 | Ehrenkranz |

OTHER PUBLICATIONS

International Search Report and Written Opinion for PCT/US2018/061841 dated Mar. 13, 2019.

Fig. 1 Background

DATA COLLECTION AND ANALYTICS BASED ON DETECTION OF BIOLOGICAL CELLS OR BIOLOGICAL SUBSTANCES

BACKGROUND

In biology, a cell is the basic structural, functional, and biological unit of all known living organisms. A cell is the smallest unit of life that can replicate independently, and cells are often called the "building blocks of life." The term "cell" itself is very common. Herein, the term "biological cell" is used to distinguish the term from other common uses in other fields.

Typically, biological cells consist of cytoplasm enclosed within a membrane, which contains many biomolecules such as proteins and nucleic acids. Organisms can be classified as single-celled or unicellular (consisting of a single cell; including bacteria) or multicellular (such as plants and animals). While the multicellular plants and animals are often visible to the unaided human eye, their individual cells are visible only under a microscope, with dimensions between 1 and 100 micrometers.

Common examples of biological cells are microbes. Microbes (i.e., microscopic organisms) are microscopic living things that are found nearly everywhere on our planet. Indeed, macroscopic living things (e.g., humans) normally co-exist peacefully with microbes. Indeed, many microbes are helpful or essential to a healthy life and a healthy ecosystem.

Unfortunately, some microbes are harmful microorganisms. These are typically called pathogens. A bacterium is an example of a pathogen that may infect a human and produce disease. For example, *Listeria* produces listeriosis and *Staphylococcus* produces a staph infection.

Modern hygiene and sanitation techniques and technology have greatly reduced the chances of encountering pathogens. However, they have not eliminated the risk. Indeed, many people still fall ill or worse by coming in contact with pathogens. Often, these pathogens are transferred from one surface (e.g., countertop) to another (e.g., a hand) by surface contact.

Since microbes, by their nature, are too small to be seen by the unaided eye, a person is unaware of the relative cleanliness of a surface before touching that surface. Since all typical surfaces have some microbes thereon, a person is typically unable to know how much or what kind of microbes are on a surface.

SUMMARY

Described herein are techniques related to the data collection of and/or analytics based on the detection and/or identification of biological cells and/or substances. This summary is submitted with the understanding that it will not be used to interpret or limit the scope or meaning of the claims.

BRIEF DESCRIPTION OF THE DRAWINGS

The Detailed Description references the accompanying figures. In the figures, the left most digit(s) of a reference number identifies the figure in which the reference number first appears. The same numbers are used throughout the drawings to reference like features and components.

DETAILED DESCRIPTION

Figure 1:
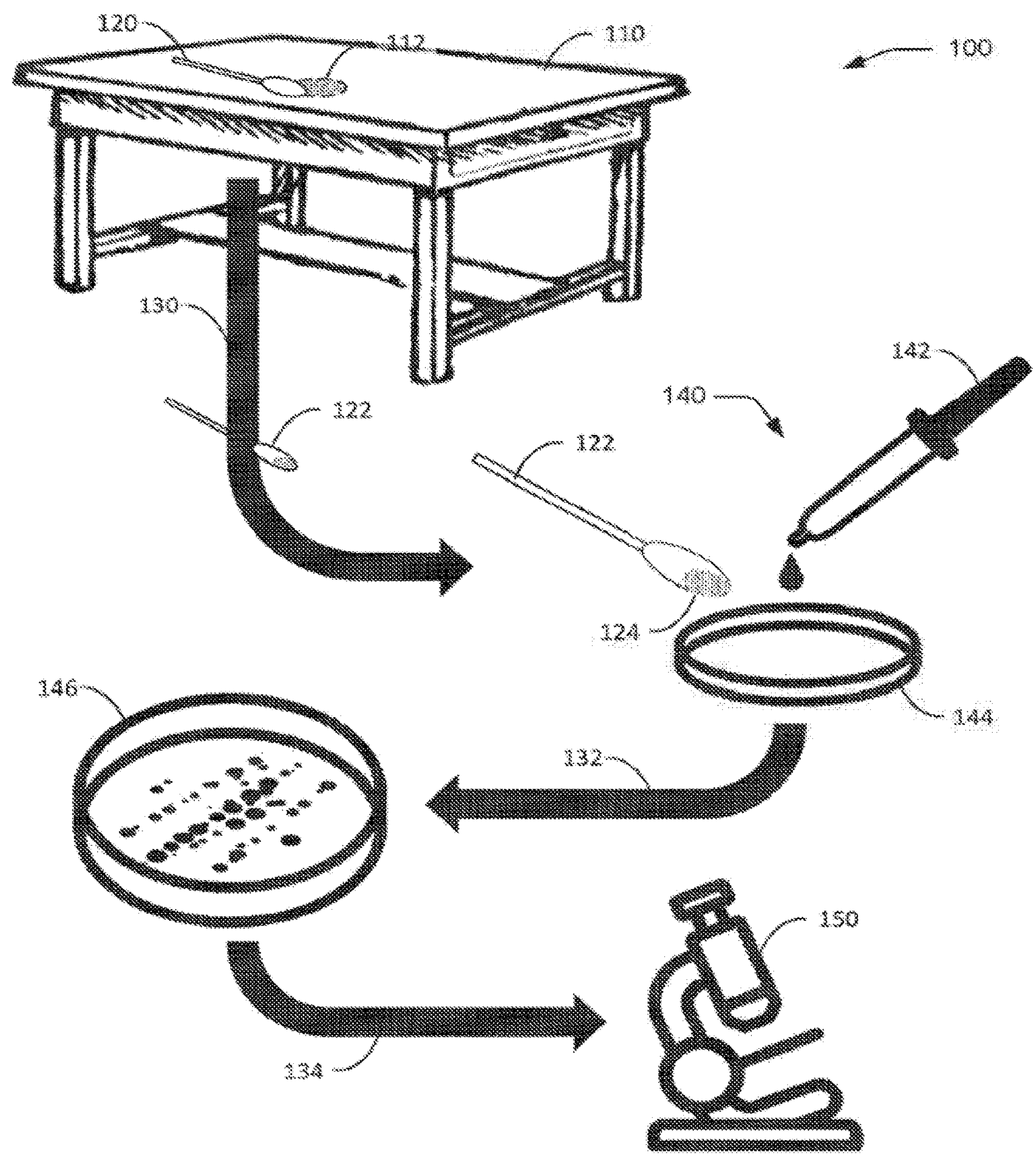
FIG. 1 illustrates conventional techniques to detect and identify pathogens.

Disclosed herein is technology to facilitate the data collection of and/or analytics based on the detection and/or identification of based on the detection and/or identification of biological cells and/or substances. Based on the analysis of the collected data, various and multiple different types of correlations may be determined, and inferences calculated therefrom. For example, epidemics of infectious diseases may be detected in their embryonic stages and actions triggered to block its spread.

In some implementations, this detection and/or identification of pathobiological cells and/or substances are performed in situ (i.e., in place) and without any interference, contact, or adulteration by the tester or testing equipment. Thus, the technology described herein can facilitate the detection of and the nature of the threat of the spread of disease where and when the threat exists. With the in situ implementations, the detection and/or identification occurs in the field. That is, it does not rely on later and further testing at another location, thus it is in-the-field.

In addition, with the technology described herein, diseased cells (e.g., cancerous) can be detected and identified. In some implementations, the cells may be detected or identified on or inside a human body (which is an example of in situ) and without any interference, contact, or adulteration by the tester or testing equipment. Thus, the technology described herein can facilitate the detection of and the nature of the actual disease (e.g., cancer) where it hides on or in the human body. This detection does not rely on later and further testing at another location, thus it is in-the-field.

The detection and identification of pathogens (i.e., disease-causing) and pathological (i.e., diseased) cells is an important application of the technology described herein, but it is just only one application. More generally speaking, this technology may be used to study cells both in-the-field and in real time. More particularly, cells may be studied to determine what changes over time, discover correlations from those changes, and draw inferences from those correlations.

In this way, the cells being studied need not be pathobiological. They may be any cells. In particular, the subject cells may be ones where it would be desirable to study them in their natural environment rather than cultured in a lab, where it would be desirable to study them in real time. Herein, real time involves cells life cycle in their normal course rather than cultured as they are typically done in a lab.

In other implementations of the technology described herein, disease-causing cells (e.g., pathogens) or disease-causing substances (e.g., toxins) may be detected or identified in situ or "in the lab." As used herein, the term "in the lab" refers to the opposite of in situ. While the action may literally occur in a lab, the term more broadly refers to these actions (e.g., detection and identification) occurring not in place, not in the field, away from the location where the cells or substances are discovered, or with interference, contact, or adulteration by the tester or testing equipment. For example, growing collected cells in a petri dish occurs in the lab.

The hardware may include a system-on-a-chip (SoC) to be used in various devices, such as the Internet of Things (IoT) develops. The chip may be based on various architectures, such as RISC architectures, for example, Arm Limited based architectures. The chip can collect molecular data in real time, increasing the amount of available data by orders of magnitude.

An implementation using SoC may greatly reduce the data bandwidth required to be transmitted to the platform. Especially, when SoC is used for using object detection and identification processing.

Example Scenario

*Listeria monocytogenes* is a pathogen that causes listeriosis, which is an infection with symptoms of fever, vomiting, and diarrhea. This pathogen is an example of a pathobiological cell. *Listeria* can spread to other parts of the body and lead to more serious complications, like meningitis. *Listeria* is often transmitted by ready-to-eat foods, such as milk, cheese, vegetables, raw and smoked fish, meat, ice cream, and cold cuts. This early and rapid detection is desirable so that cross-contamination can be avoided, and any problems immediately addressed.

These ready-to-eat foods are often mass produced in food factories. In these factories, there is little to no time to stop production to test to determine if a harmful pathogen (like *Listeria*) exists on the food-production surfaces. Depending on the comprehensiveness and desired accuracy of the test, conventional techniques to detect the bacteria take as long as a week to as short as hours. Regardless of the particulars of the test, these conventional tests involve the manual collection of samples from various surfaces, cataloging these samples, and performing invasive testing (e.g., culturing, chemical reaction, antibodies, etc.).

FIG. 1 Illustrates conventional techniques 100 to detect and identify pathogens. Table 110 has a surface that, of course, has microbes thereon. This table 110 represents anything with a surface area that might have microbes living on it. For this discussion, assume that table 110 is in a commercial kitchen of a ready-to-eat food manufacturer. This manufacturer is concerned about *Listeria* in this kitchen. To detect the existence of *Listeria* in its kitchen, the manufacturer orders spot tests be performed in the kitchens.

To that end, a spot 112 on table 110 is selected for sampling. Using a sample-collection swab 120, a tester swipes the spot 112. Following arrow 130, a sample-collected swab 122 is carefully transported to a testing station 140 so as to avoid collateral and inadvertent collection of samples from other sources.

Typically, this testing station 140 is physically separated and distant from the sample spot 112 of the commercial kitchen where the sample was collected. The testing station 140 is often in a laboratory of a testing facility. With traditional methods, the sample microbes 124 of the sample-collected swab 122 are transferred to Petri dishes 144 for cultivation. At some point, chemicals 142 may be added to the cultured microbes of the Petri dishes 144 for various reasons, such as dyes to make them more visible.

Following arrows 132 and 134 and perhaps weeks or months, a petri dish 146 with the adultered (e.g., dyed) cultured microbes is ready to be examined under a microscope 150. Typically, a human examines the cultures under the microscope 150 and identifies pathogens amongst the cultured microbes based on many factors, but mostly the human's professional experience in identifying such microbes.

Traditional methods of testing like that demonstrated in FIG. 1, where sample microbes are cultivated in labs, are flawed. 'Stressed' cells will not grow in cultures (and will, therefore, produce negative results) despite the bacteria being present, live and potentially harmful. Also, this is the slowest form of testing.

Alternative conventional techniques, based on molecular/chemical methods, detect all cell types, but don't differentiate between live and harmless dead cells, which can remain after disinfection. Thus, these molecular/chemical methods may indicate a false positive for the presence of a pathogen when only dead cells of the pathogen are present.

Still, other conventional techniques use antibodies to test biofilms, which are groups of microbes where cells stick together on a surface. This technique requires the biofilms to be removed from the surface, treated with a particular antibody, and then tested to see if the biofilm fluoresces. This type of technique only tests for the particular pathogen that the introduced antibody interacts with.

Example Electronic Device

Figure 2:
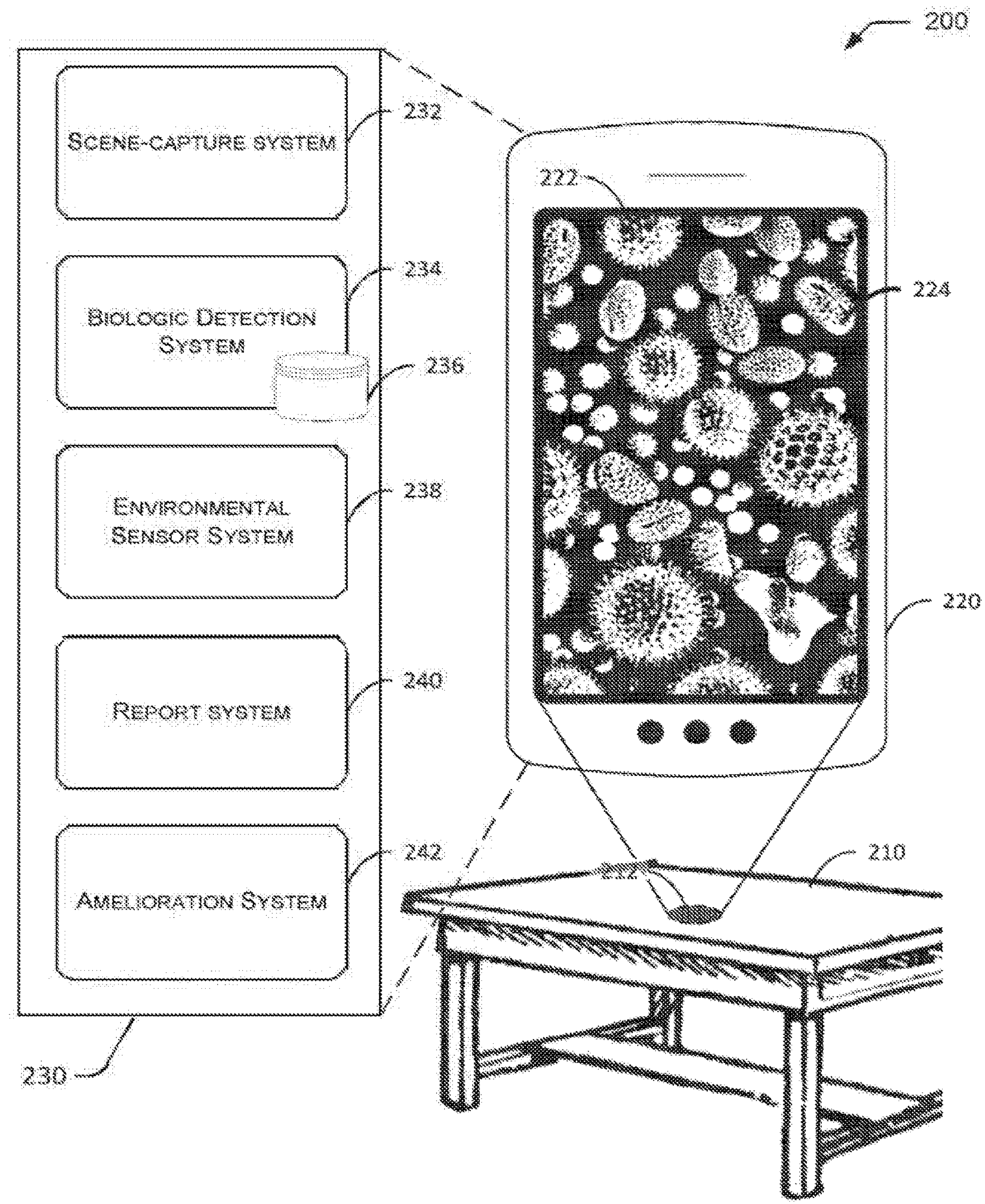
FIG. 2 illustrates an example system in accordance with the present disclosure.

FIG. 2 illustrates an example scenario 200 in accordance with the technology described herein. The example scenario 200 includes a table 210. That table has a scene 212, which is an area of a surface in view of a camera (not shown) of a smartphone 220. Indeed, the camera captures an image 222 of scene 212. Just like reality, the scene 212 includes multiple microbes, but these microbes are not visible in scene 212.

For the example scenario 200, the microbes are described as in situ (i.e., in place) because they are examined, tested, etc. where they naturally live, inhabit, or exist. That is, the microbes are not in the lab. Herein, "in the lab" indicates that the microbes have been moved, relocated, or expatriated in order to perform the examination, testing, or the like. Other implementations of the technology described herein may involve microbes that are in the lab.

That image 222 is depicted as being viewed on a display of the smartphone 220. The image 222 has been sufficiently magnified to be able to see various in situ microbes of scene 212. And while not yet detected, one of these microbes is a pathogen 224.

The smartphone 220 is one example of an electronic device 230 in accordance with the technologies described herein. However, in other example scenarios, the electronic device 230 may be, for example, a tablet computer, a smartdevice, a standalone device, a collection of cooperative devices, a button-sized device, a device on a chip, an accessory to a smartphone or smartdevice, an ambulatory device, a robot, swallowable device, an injectable device, embedded within medical lab equipment, or the like.

As depicted, the electronic device 230 includes a scene capture system, a biologic detection system (and object detection system) 234, a database 236, an environmental sensor system 238, a report system 240, and an amelioration system 242. These systems of the electronic device 230 are constructed from hardware, firmware, special-purpose components (e.g., sensors), and/or some combination thereof. These systems may, in some instances, include software modules as well.

The scene-capture system 232 is designed to obtain an image (e.g., image 222) of a scene (e.g., scene 212) that includes in situ biological cells therein. That is, there are biological cells located in a place (i.e., in-the-field) in the scene that is being captured by the scene-capture system. In some implementations, the scene-capture system 232 includes a camera to capture the visible part of the electromagnetic spectrum that is emitting or reflecting from the matter contained in the scene. In some implementations, the scene capture system 232 includes components designed to capture non-visible parts of the electromagnetic spectrum (e.g., x-rays, infrared, gamma rays, ultraviolet, etc.) that is emitting or reflecting from the matter contained in the scene.

Examples of the action of obtaining (as performed by the scene-capture system 232) include measuring, collecting, accessing, capturing, procuring, acquiring, and observing. For example, the scene capture system 232 may obtain the image by capturing the image using the charge-coupled device (CCD) of the digital camera. In another example, the scene-capturing system 232 may obtain the image by measuring the electromagnetic spectrum of the scene.

The obtained image is micrographic, spectrographic, digital, or some combination thereof. The obtained image is micrographic because it captures the elements in the scene that are on a microscopic scale. The obtained image is spectrographic because it captures elements in the scene by using equipment sensitive to portions of the electromagnetic spectrum (visible and/or non-visible portions). The obtained image is digital because it formats and stores the captured information as data capable of being stored in a machine, computer, digital electronic device, or the like.

While the thing that is captured is called an image, this image is not necessarily displayable as a two dimensional depiction on a display screen (as shown in image 222). Rather, the image an array of data that represents the quantitative and qualitative nature of the electromagnetic spectrum (or some portion thereof) received by the components of the scene capture system 232 when it was exposed to the scene (e.g., scene 212).

The biologic detection system 234 is designed to analyze the obtained image and detect the presence of one or more pathobiological cells amongst the in situ biological cells of the captured scene. In some implementations, the biologic detection system 234 may actually identify one or more particular cells and/or substances in the scene. In that case, it may be called a biologic identification system. Such a system may identify the particular pathobiological cells amongst the in situ biological cells. Thus, depending on the implementation, this system 234 may be referred to as biological-cell detection system or the pathobiological detection system.

To accomplish detection, the biologic detection system 234 may employ on and/or employ a database 236. This database 236 may be a database of pathobiologic-cellular signatures or training corpus. The biologic detection system 234 is a particular example of a biologic-cellular detection system. A training corpus is a database of numerous application-specific samples from which the AI/ML/DL engine "learns" and improves its capabilities and accuracy.

The biologic detection system 234 employs an AI/ML/DL engine to perform or assist in the performance of the detection and/or identification of one or more pathobiological cells. AI/ML/DL is short for artificial intelligence/machine learning/deep learning technology. Particular implementations may employ just an AI engine, just an ML engine, just a DL engine, or some combination thereof.

The AI/ML/DL engine may be implemented just on the smartphone 220 itself. In that case, the smartphone 220 need not communicate in real time with the platform (e.g., a remote computing system). In another implementation, the AI/ML/DL engine may be implemented just on the platform (thus remotely). In that case, the smartphone 220 communicates in real time for nearly so) with the platform (e.g., a remote computing system). In still other implementations, the AI/ML/DL engine is implemented partially in both the smartphone 220 and the platform. In this way, the intensive processing is offloaded to the platform.

Some implementations of the biologic detection system 234 may perform its data analysis solely on the device without assistance from other devices, servers, or the cloud. Other implementations of the biologic detection system 234 may farm out all or nearly all of the data analysis to other devices, servers, or the cloud. In still other implementations, the data analysis may be shared amongst multiple devices and locations.

On its own or working with other devices or computer systems, the biologic detection system 234 analyzes the image of the scene to detect, determine, and/or identify the type or class of biological cells therein. It may do this, at least in part, by using distinguishing molecules of the cells that are observable using the electromagnetic spectrum. Is some implementations, other data (such as chemical reactions or excitation) may be included in the analysis.

Some of these molecules are indicative of certain classes, types, or particular cells. Such molecules are called marker biomolecules herein. The electronic device can determine which cell types or class are present in a captured scene by the on the particular ones of, the types of, and the proportions of the biomolecules detected therein. This may be accomplished, at least in part, by calculating probabilities of objects detected in the image.

The environmental sensor system 238 is designed to measure one or more environmental factors associated with the in situ biological cells or the environment surrounding the in situ biological cells. In some instances, the environmental sensor system 238 may be simply described as a sensor.

The report system 240 is designed to report detection and/or identification of the one or more pathobiological cells in the obtained image and in some implementations, the report system 240 is designed to associate the measured environmental factor with the obtained image and/or with the detected pathobiological cell.

The amelioration system 242 is designed to respond to the detection and/or identification in a manner that ameliorates the pathobiological nature of the detected/identified pathobiological cells.

The electronic device 230 may have a communications system to send or receive data from other similar electronic devices or centralized/distributed servers. The electronic device 230 may have enhanced processor or co-processor to perform image-capture and processing functions.

Of course, the example scenario 200 described above is one implementation that detects pathobiological cells. Other implementations of the technology described herein may detect or identify pathobiological substances rather than cells.

One or more of the systems of electronic device 230 may be characterized as a non-transitory computer readable storage medium comprising instructions that when executed cause one or more processors of a computing device to perform the operations of that electronic device.

Pre-Processed Data

Typically, images of the same scene are captured over time. That may be over a few seconds, few minutes, or perhaps a few hours. In so doing, a massive amount of raw image data is produced. So much data that it may quickly overwhelm the local storage capacity of the smartphone 220 and often overwhelms the data transfer rate between the smartphone 220 and any network-based storage solution.

To address this issue, the smartphone 220 maybe designed to pre-process or process the raw scene-captured data before storing locally or transferring it across the network. For pre-processing, the smartphone 220 may derive just the most critical or key data that helps identity or reconstruct the scene.

For example, the smartphone 220 may store the marker biomolecule information from each captured image or scene. The marker biomolecule information includes just the data regarding the type, amount, proportions, etc. of the marker biomolecules or substances detected, determined, identified, etc. in a particular image or scene. Thus, any other data from the image capture is discarded.

Along with associated environmental factors, this pre-processed information is stored or transferred across the network. This reduces the data storage/transfer requirements by multiple orders of magnitude. The particular cell type or class is determined from this stored or transferred pre-processed data. This may be done later or by different systems.

In some instances, the smartphone 220 may fully process the image/scene captured data to determine, detect, and/or identify the cell type or class. In this scenario, the electronic device stores or transfers its conclusion about the cell type or class with its associated environmental factors.

Scale of Amount of Data

Since the images being captured are on a microscopic scale, it may take many images to capture a small surface area of an object. In addition, even a short sequence of images adds up quickly to a great multitude of images. Thus, in only a short space (e.g., of just a few seconds), the sequence of microscopic-scale images of a very small area quickly overwhelms the internal data transfer, data storage, and/or data processing capability of a typical electronic device (such as a smartphone). In addition, the typical external data transfer rates (e.g., of wireless communication) is not capable of accepting the data tsunami of this technology.

Two example approaches may be employed to address these issues. One involves the increased capacity of the electronic device, and the other involves the processing of the data into a manageable form.

First, this technology is implemented in such a way to employ special-purpose hardware to perform the pre-processing and processing of the incoming real-time data. That is, the specially designed hardware is built directly into the processors and electronics of the device to enable the device to quickly process the massive amount of incoming real-time data into a representative portion thereof without losing important aspects of the data.

Second, this technology employs a particular mechanism to produce a representative portion thereof without losing important aspects of the data. In short that involves saving the deltas (i.e., changes) between the measurements (e.g., marker biomolecules) over time. These deltas are stored and/or transferred. In addition, data compression schemes may be used.

Imaging

The technology described herein utilizes an image-capturing system, such as the scene-capture system 232. In some instances, the image-capturing system may be called a camera. This is particular so when the system captures the visible part of the electromagnetic spectrum that is emitting and/or reflecting from the matter being observed. In some implementations, the image-capturing system may capture non visible parts of the electromagnetic spectrum (e.g., x-rays, gamma rays, ultraviolet, etc.) that are emitting or reflecting from the matter being observed.

With some implementations, the image-capturing system may employ hyperspectral imaging and, in particular, snapshot hyperspectral imaging. Hyperspectral imaging collects and processes information from across a portion of the electromagnetic spectrum. With hyperspectral imaging, the spectrum is captured for each pixel in the image of a scene. Snapshot hyperspectral imaging uses a staring array (rather than a scanning array) to generate an image in an instant.

With some implementations, the image-capturing system may employ light-field imaging, which is also called plenoptic imaging. A plenoptic imaging system captures information about the light field emanating from a scene. That is, it captures the intensity of light in a scene, and also the direction that the light rays are traveling in space. This contrasts with a conventional camera, which records only light intensity.

Using plenoptic imaging enables the simultaneous capture of pictures at different focal points, allowing the device sensor to capture a two-dimensional image in multiple 3rd dimension planes (i.e., capture a volume of space vs. a plane). Capturing a volume facilitates faster detection on non-flat surfaces or when fluids or gases are observed.

In addition, a combination of both these hyperspectral and plenoptic technologies may be used. That is, the image-capture system may incorporate both snapshot hyperspectral imaging with plenoptic imaging.

Nanophotonics

In some instances, an agent is purposefully introduced into the scene, environment, or in the lab to enhance or improve the observations or measurements. For example, photonic nanostructures may be spread in the environment where measurements and observations may be made.

These photonic nanostructures are part of a field called nanophotonics or nano-optics, which involve is the study of the behavior of light on the nanometer scale, and of the Interaction of nanometer-scale objects with light. It is a branch of optics, optical engineering, electrical engineering, and nanotechnology. It often (but not exclusively) involves metallic components, which can transport and focus light via surface plasmon polaritons.

The term "nano-optics," just like the term "optics," usually refers to situations involving ultraviolet, visible, and near-infrared light (free-space wavelengths from 300 to 1200 nanometers).

Using nanophotonics to create high peak intensities: If a given amount of light energy is squeezed into a smaller and smaller volume ("hot-spot"), the intensity in the hot-spot gets larger and larger. This is especially helpful in nonlinear optics; an example is surface-enhanced Raman scattering. It also allows sensitive spectroscopy measurements of even single molecules located in the hot-spot, unlike traditional spectroscopy methods which take an average over millions or billions of molecules.

One goal of nanophotonics is to construct a so-called "superlens", which would use metamaterials or other techniques to create images that are more accurate than the diffraction limit (deep subwavelength).

Near-field scanning optical microscope (NSOM or SNOM) is another nanophotonic technique that accomplishes the same goal of taking images with resolution far smaller than the wavelength. It involves raster-scanning a very sharp tip or very small aperture over the surface to be imaged.

Near-field microscopy refers more generally to any technique using the near-field to achieve nanoscale, subwavelength resolution. For example, dual polarization interferometry has picometer resolution in the vertical plane above the waveguide surface.

Environmental Factors

As indicated above, sensors obtain environmental factors related to, about, or near the scenes being observed. These may be called ambient factors. The sensors may measure or sense to obtain the environmental factors. In other instances, the factors may be accessed, acquired, procured, etc. via another source, sensor, memory, machine, etc.

The environmental factors are abiotic or biotic. However, there are other datapoints that may be gathered, but which are not expressly related to the environment. These may be called associated or observation-related factors.

An abiotic environmental factor is associated with non-biological sources. That is, the source of the thing being measured is not related to a living or recently living thing.

Examples of abiotic environmental factor include ambient temperature, timestamp (e.g., time and date), moisture, humidity, radiation, the amount of sunlight, and pH of a water medium (e.g., soil) where a biological cell lives. Other examples of abiotic environmental factors include barometric pressure; ambient sound; indoor location; ambient electromagnetic activity; velocity; acceleration; inertia; ambient lighting conditions; WiFi fingerprint; signal fingerprints; GPS location; geolocation; airborne particle counter; chemical detection; gases; radiation; air quality; airborne particulate matter (e.g., dust, 2.5 PPM, 10 PPM, etc.); atmospheric pressure; altitude; Geiger counter; proximity detection; magnetic sensor; rain gauge; seismometer; airflow; motion detection; ionization detection; gravity measurement; photoelectric sensor; piezo capacitive sensor; capacitance sensor; tilt sensor; angular momentum sensor; water level (i.e., flood) detection; flame detector; smoke detector; force gauge; ambient electromagnetic sources; RFID detection; barcode reading; or some combination thereof.

A biotic environmental factor is one having a biologic source. Example of such include the availability of food organisms and the presence of conspecifics, competitors, predators, and parasites.

While it is not an environment factor, per se, the observation related or associated factor is described here. The associated or observation-related factor may be a measurement of quality, quantity, and/or characteristic of the environment about the observation itself or related to the environment from which the subject is observed or was obtained. They may also be data that a human or computer associated with other environmental factors or the scene.

Examples of the observation-related or associated factor include nearby traffic patterns or noises, tracking the movements of particular individuals (e.g., via employee badges or security cameras); visitors; patients, budgets of related departments; and the like.

Herein, a known sensor or measurement device may be listed as an example of an environmental factor. For example, Geiger counter and seismometer are listed as examples. It should be understood that the relevant factor for least listed examples is the measurements typically made by such devices. Thus, the obtained factor for example Geiger counter is radiation and the obtained factor for the example seismometer is the motion of the ground.

Artificial Intelligence, Machine Learning, and Deep Learning Technology

Herein, the term AI/ML/DL technology refers to a technology that employs known or new artificial intelligence (AI) techniques, machine learning (ML) techniques, deep learning (DL) techniques, and/or the like.

By applying AI/ML/DL technology such as convolutional neural networks (CNNs), some implementations of the technology described herein is capable of identifying pathobiological cells and substances within microscopic images and spectrographic signatures that environment and systems ingest from either existing datasets or streams of real-time sensor data.

By training its neural networks against libraries of high-quality pathobiological cells/substances images and signatures, the technology described herein can reliably identify specific cells/substances. Upon discovery, the technology described herein may take advantage of a sophisticated queueing system to retroactively "replay" historical data with a greatly increased sampling rate, enabling it to build a high-resolution model of the outbreak. This model is then added to the chain, fully secure, attributed and available to researchers who can use it to help contain the outbreak or to advance the understanding of its transmission model.

For example, the technology described herein can provide for real-time and real-world data. The chip is used in the data ingest pipeline and marketplace. Deployed throughout a building and/or across a region and using the sensor technology to pick up environmental (e.g. temperature, humidity, etc.), visible, and spectrographic data which, coupled with ambient other (e.g., location, time, etc.) data, the numerous chips in the system can together stream enormous volumes of valuable data into the platform for processing by the artificial intelligence insights engine described herein. As used herein, a platform includes a remote device with massive storage capacity and processing power.

The technology described herein may utilize AI to detect objects that have already been learned by a device or platform implementing the technology. This minimizes the amount of data transmitted, efficiently utilizing communication bandwidth. The sensed and other data associated with objects that the technology described herein detects, but cannot identify, will be sent to the platform which would, in turn, trigger an investigation that gathers real world samples and take those samples to a lab for controlled analysis and identification using machine learning with deep learning. Once identified in the lab, the platform can send a specific detection approach to an implementation of the technology described herein so that it can then confidently identify the new object is going forward.

The technology described herein will either contain or connect to sensors that will enable novel abilities to detect pathobiological cells and substances at low concentrations, in noisy environments (e.g. objects in the midst of dust, dirt, or other uninteresting objects), in real-time (e.g. without significant delay from when object was in field of view), in some cases without disturbing the environment detected objects (i.e. passive observation), and with the ability to search large three dimensional spaces so as to reduce the probability of not observing an interesting object which is especially important when the objects are infrequently present.

Having some or all of these qualities, coupled with detection assisted by AI/ML/DL engines will facilitate detection and identification that is much faster than present technology, more accurate, and possible outside of a lab environment.

Some implementations of the technology described herein utilize AI/ML/DL technology in the detection or identification of pathobiological cells or substances from collected data. In other implementations, the technology descried herein may utilize AI/ML/DL technology in the analysis of the collected data with metadata such as environmental factors collected therewith.

According to Apr. 4, 2018, cloudmayo.com article ("Difference between Artificial Intelligence, Machine Learning and Deep Learning"), there is much confusion between three different but interrelated technologies of AI, ML, and DL. The article defines AI as a "technique that allows a computer to mimic human behavior," ML as a "subset of AI techniques that uses a statistical method to enable a machine to improve with experiences," and DL as a "subset of ML which makes the computation of multi layer neural networks feasible."

The electronic component or collection of components that employs an AI/ML/DL technology for training and/or data analysis is called an AI/ML/DL technology herein.

System-on-a-Chip

Figure 3:
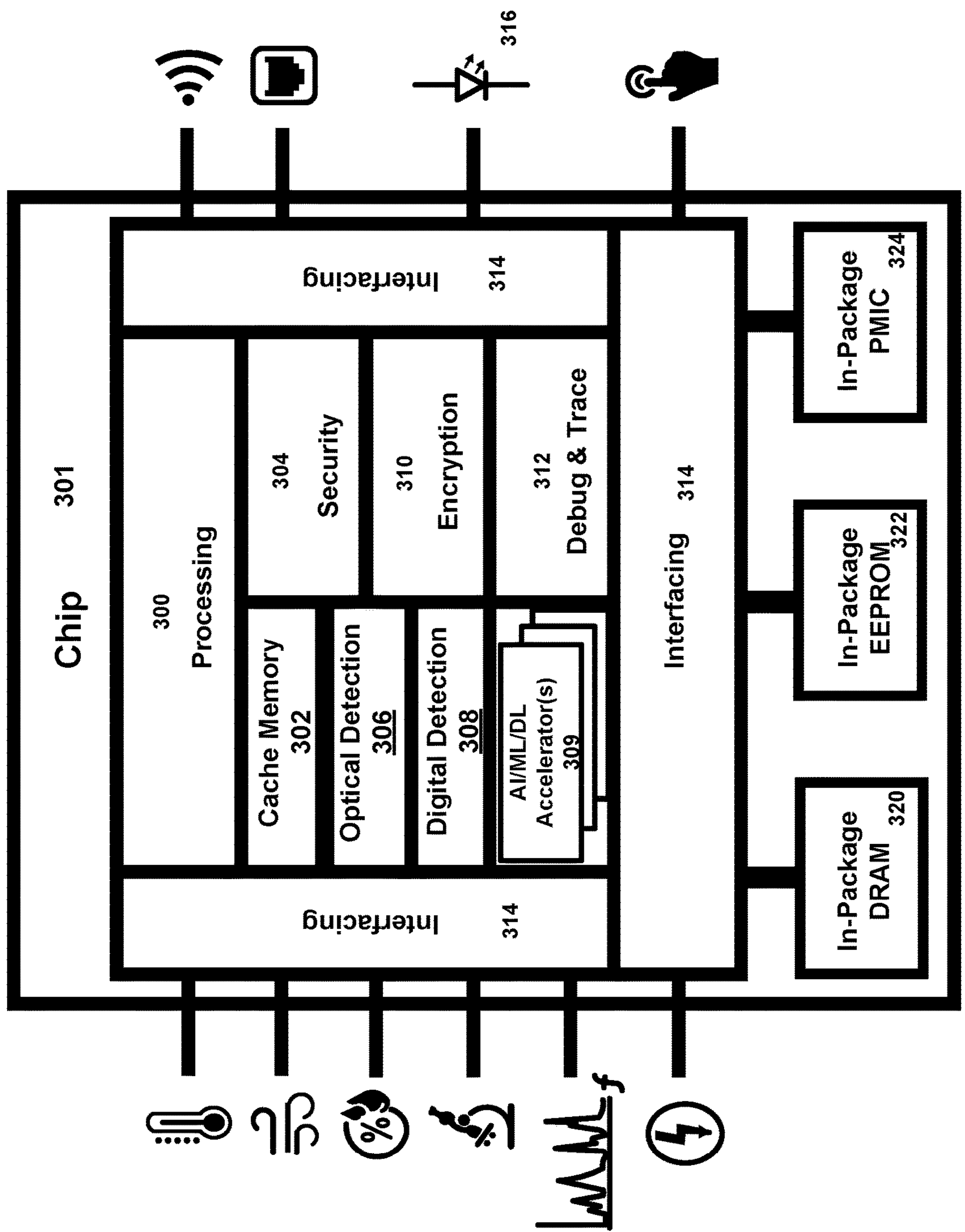
FIG. 3 illustrates a chip architecture in accordance with the present disclosure.

FIG. 3 illustrates an example system-on a-chip 400, which is an implementation of the technology described herein. As shown, the system-on-a-chip 400 include a semiconductor chip integrated into a single package or as a chipset 301. Although a particular chip architecture is described, it is to be understood that other semiconductor chip architectures may be implemented.

The chip 301 can be resident in different devices, such a smart phones, laptop/table computers, dedicated medical/research devices, etc. Such devices are used for detection of pathobiological cells or substances. In certain implementations, computing may be performed off-chip via the cloud, or performed on the chip.

The chip 301, and in particular devices including the chip 301, may use AI/ML/DL engines to process data. In particular, AI/ML/DL engines may be used by the chip 301 in the accelerated processing of collected data, such as environmental factors and other data to detect/identify pathobiological cells and substances. In addition, doing so reduces data bandwidth of communication (e.g., to the platform). Also, distributed processing at the device reduces the cost of the device and reduces communication bottlenecks.

The chip 301 includes a processor(s) or processing component 300, cache memory 302, security component 304, optical detection 306, and digital detection 308. Depending on the implementation, the digital detection 308 may be used for one or more of the following: digital enhancement, object detection, or object identification.

Chip 301 can include one or more AI/ML/DL engines or accelerators 309. The AI/ML/DL accelerators 309 can implement edge and/or cloud computing. Chip 301 further can include encryption 310, and debug and trace component 312.

Interfaces 314 are provided/included in chip 301. In particular interfaces 314 provide the ability to receive sensory input, such as environmental factors (e.g., temperature, air pressure, wireless signals, capacitance, etc.) and capture image of a scene (e.g., via a microscope, camera, or spectrometer). The interface 314 also allows for transmission of data, network connections, user input, status indicators, and control illumination circuitry.

Interfaces 314 may further connect, for example, to an in-package dynamic random-access memory (DRAM) 320, in-package electrically erasable programmable read-only memory (EEPROM) 322, and power management integrated circuit (PMIC) 324.

Network of Monitoring Devices

Figure 4:
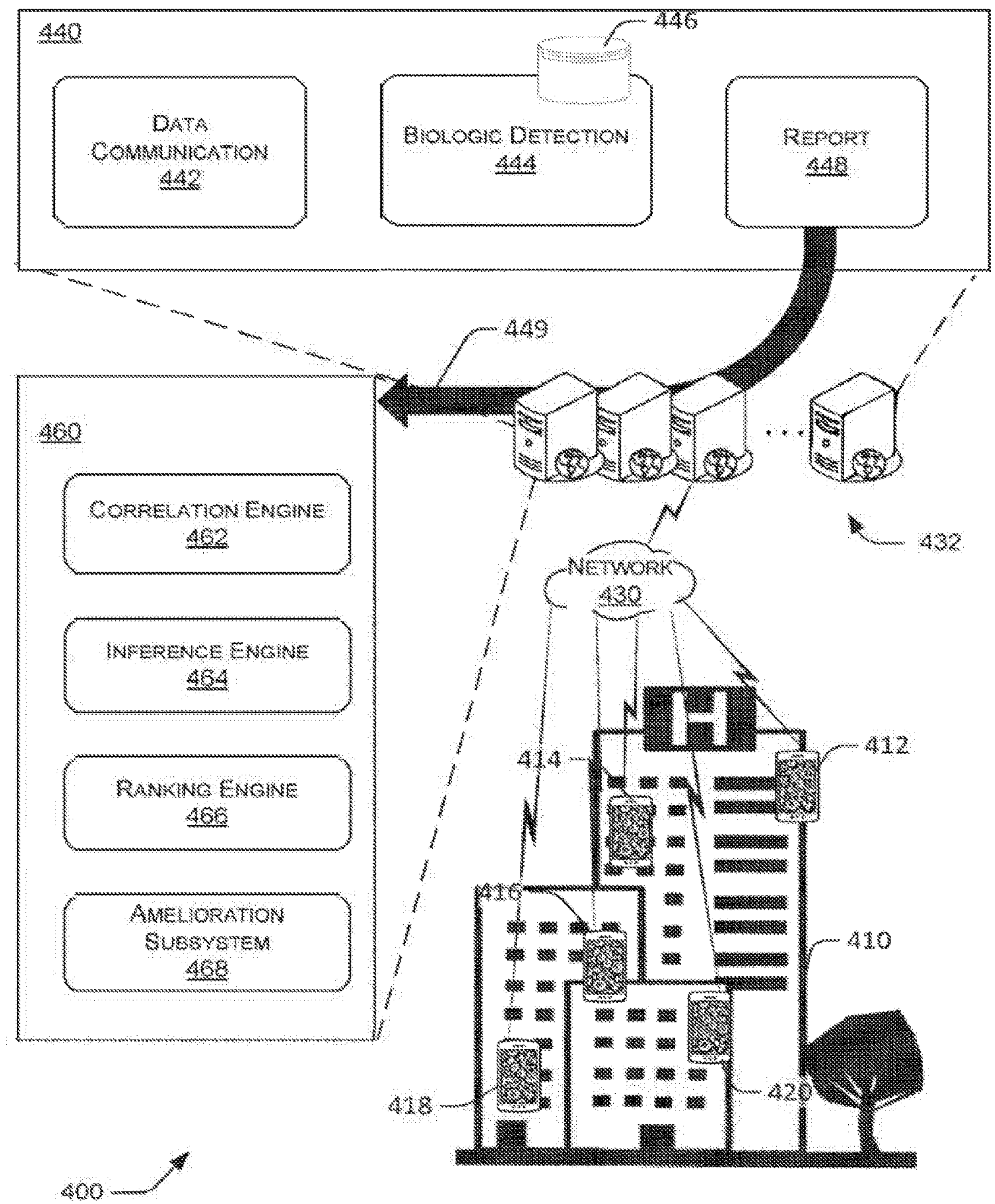
FIG. 4 illustrates an example system in accordance with the present disclosure.

FIG. 4 is an illustration of an infrastructure 400 that facilitates data collection and data analysis of the technology described herein. The data collection, for example, may occur across a network of various widths (i.e., horizontally) and depths (i.e., vertically). Consider for this example a single building. That building is called the Hope Hospital 410.

The Hope Hospital 410 has many different floors, rooms, departments, etc. For illustration purpose, the Hope Hospital 410 has four floors of five rooms each. And each floor is a department.

The Hope Hospital 410 has installed a variety of electronic monitoring devices. These devices are like smartphone 220 of example scenario 200. However, these electronic monitoring devices may be stationary and special-purpose. These electronic monitoring devices are called NANOBOT™ devices herein. However, these NANOBOT™ devices are special-purpose devices rather than a smartphone. That is, the NANOBOT™ devices are designed and built for the specialized and particular purpose of the functionality described herein.

In this example, there are multiple NANOBOT™ devices placed throughout the hospital. Indeed, there could be multiple devices in each room. For example, a NANOBOT™ device may be installed on the bed, the bathroom counter, hand sanitizer dispenser, the faucet handle, the air vent, and the like. In addition, other NANOBOT™ devices may be installed in the ductwork of the HVAC.

As depicted, stationary device 412 is mounted on the wall in a room of patient X, device 414 is on the ceiling of a room of patient Y, device 416 is on the bed of patient Z, device 418 is mounted is in the ducting of the third floor, and device 420 is a portable device carried by a nurse.

Each of these NANOBOT™ devices are installed to monitor biological cells and/or substances and environmental factors in their proximity. The devices will detect and/or identify the particular cells and/or substances in their proximity. In addition, the ongoing monitoring of these devices enable the tracking of changes in the detected and/or identified microscopic lifeforms, for example, in their proximity.

In addition, each of these NANOBOT™ devices include a sensor or sensors for monitoring one or more environmental factors, such as ambient temperature, humidity, indoor location, and the like. Each device tracks its proximate factors and microscopic lifeforms over time.

In addition to the stationary NANOBOT™ devices, other electronic devices may be used in the Hope Hospital 410. For example, there may be mobile or ambulatory devices that are specially designed to do the same functions. These devices may be affixed to a mobile or portable platform. Alternatively, these devices may have the ability to relocate on their own power or volition.

For example, NANOBOT™ device may be affixed to a cart, robotic medication dispenser, a chart, and the like. As such, the NANOBOT™ device tracks the environmental factors and biological cells proximate the device as the thing to which it is affixed is moved throughout the hospital. As such, the indoor location of the device changes as well.

Similarly, a NANOBOT™ device may have its own mechanism for self-propulsion. It may have electric motors, wheels, and self-navigational capability to travel the hallways, walls, and ducts of the building. In addition, some self-propelled NANOBOT™ devices may travel in the air, for example, like a so-called drone (i.e., unmanned aerial vehicle). In some instances, a self-propelled NANOBOT™ device may travel on and/or within liquid.

The self-propelled NANOBOT™ device may wander around the hospital or other space to generate a comprehensive amount of monitoring data for such space or a portion thereof. Alternatively, the self-propelled NANOBOT™ device may travel a pre determined path or navigate its own path. In doing so, the device is tracking data as it travels and/or at particular points along the path.

In addition, humans may carry smartphone or some form of smartphone accessory (e.g., watch) that is capable of performing these functionalities. Indeed, this type of mobile device may perform these functions actively and/or passively. That is, the user may actively choose when and where to perform measurements, and/or the device may choose when and where to perform measurements.

These various devices in the Hope Hospital 410 may be interconnected with each other and/or connected to a common or interconnected network 430. For example, the stationary NANOBOT™ devices may be connected to each other view a peer-to-peer mesh wireless network. Devices may be connected via a wireless access point (WAP) or via short-range wireless signal (e.g., BLUETOOTH). In turn, these networks may be connected to other networks (such as the so-called Internet) and to centralized or distributed computing center. For example, all of the stationary NANOBOT™ devices in a room may be connected at a single nearby WAP that is connected to the so-called cloud where the acquired data is stored in a cloud-based storage system. The network 430 represents any and all of these suitable communication networks.

Data Collection

Each device in the Hope Hospital 410 is configured to monitor its proximate area. The devices monitor for biological cells and various environmental factors, such as location, temperature, and humidity. Each device may be configured to collect data in a manner like that smartphone 220 of example scenario 200.

Once the data is collected by a monitoring device, it may be locally analyzed, or the raw data may be transferred or uploaded to a centralized and/or distributed computing system. Supersystem 432 is depicted as a several servers. This represents the centralized and/or distributed computing system.

If analyzed locally, the collected data may be fully or partially analyzed locally. With local analysis, some or all of the processing that is necessary to detect and/or identify a class or type of biological cell is performed on the monitoring electronic device. Indeed, if fully processed locally, the monitoring device may form a conclusion regarding the type/class of cell in a monitored scene.

In some instances, the raw monitor data or partially processed data may be uploaded or transferred to a computing system. For example, each floor of the Hope Hospital 410 may have its own dedicated computer to store monitor data of the devices of that floor. That floor computer may perform some or all of the calculations needed to determine that type/class of the cells in the monitored scenes. Alternatively, or in addition, each building may have its own computer; each campus has its own computer; each city has its own computer; each region has its own computer; etc. Alternatively, or in addition, all of this data is transferred to the "cloud" for storage and processing overall or at each level.

In addition, individuals may collect data for their own personal reasons. For example, a visitor may collect data in the cafeteria of the hospital so that she knows how clean the surfaces are. This data and/or its analysis may be uploaded to the so-called cloud. That is, the data collection may be crowdsourced or available to the individual alone.

This data may be collected in a coordinated fashion by the Hope Hospital 410 or an agency working on their behalf. The collection and analysis of this data may be performed by the Hope Hospital 410. In addition, the collection and analysis of the data of Hope Hospital 410 may be a service that the Hope Hospital 410 subscribes to.

Furthermore, a service may collect data from many and various locations in an anonymous fashion to protect the private data of each identifiable customer. With the data collected from many different locations and customers, the service may analyze the data to find meta-trends and meta-correlations.

The supersystem 432 includes one or both systems 440 and 460. System 440 is primarily for the collection and analysis of image-based data. System 460 is primarily for the inferences or conclusions of the collected and analyzed data. The supersystem may be called the "platform" herein.

System 440 includes a data communications subsystem 442, a biologic detection subsystem 444, and a report subsystem 448.

The data communication subsystem 442 obtains (e.g., via wireless communication) image-based data from one or more of multiple remote monitoring devices. The image-based data from each monitoring device is based on (e.g., derived from) one or more images of a scene proximate to that monitoring device. The proximate scene includes biological cells and/or substances therein.

The data communication subsystem 442 also obtains (e.g., via wireless communication) environmental data from one or more of the multiple remote monitoring devices. The environmental data being based on an environmental factor associated with the in-scene biological cells and/or substances of each device or the environment surrounding the in-scene biological cells and/or substances of each device.

The biologic detection subsystem 444 analyzes the image-based data and/or the environmental data. Based on that analysis, the biologic detection subsystem 444 detects and/or identifies a type or class of biological cells and/or substance amongst the in-scene biological cells and/or substances of each device or amongst several of the devices.

To accomplish detection, the biologic detection subsystem 444 may employ on and/or employ a database 446. This database 446 may be a database of biologic cellular or biologic-substantive signatures. This may be called a training corpus. A training corpus is a database of numerous application-specific samples from which the AI/ML/DL engine "learns" and improves its capabilities and accuracy.

The biologic detection subsystem 444 employs an AI/ML/DL engine to perform or assist in the performance of the detection and/or identification of one or more biological cells and/or substances.

The AI/ML/DL engine functionality may be split across the platform. That is, the devices may perform pre-processing of the image using AI/ML/DL engine and send the results as the image-based data to the system 440 for further processing herein. In that case, the device 414 communicates in real time (or nearly so) with the platform. In this way, the intensive processing is offloaded from the devices to the platform.

The biologic detection subsystem 444 analyzes the image-based data of the scene to detect, determine, and/or identify the type or class of biological cells and/or substances therein. It may do this, at least in part, by using distinguishing molecules of the cells that are observable using the electromagnetic spectrum. In some implementations, other data (such as chemical reactions or excitation) may be included in the analysis.

The report subsystem 448 reports the detection and/or identification of the type of biological cells and/or substances in the scene proximate to the monitoring device. The report subsystem 448 may send 449 its results and associated data (image-based data and/or environmental data) to the system 460.

Data Analysis

As discussed herein, an electronic device captures a scene that has biological cells therein. In some instances, these biological cells may be described as in situ (i.e., in place) because they are monitored, examined, tested, etc. where they naturally live, inhabit, or exist. That is, the biological cells have not been moved, relocated, or expatriated in order to perform the examination, testing, or the like.

Using a camera or digital or other imaging technology, the electronic device captures a portion of the electromagnetic spectrum that is emitting or reflecting from the matter contained in the scene. The obtained image is micrographic, spectrographic, digital, or some combination thereof. The obtained image is micrographic because it captures elements in the scene that are on a microscopic scale. The obtained image is spectrographic because it captures elements in the scene by using equipment sensitive to portions of the electromagnetic spectrum (visible and/or non-visible portions). The obtained image is digital because it formats and stores the captured information as data capable of being stored in a machine, computer, digital electronic device, or the like.

While the thing that is captured is called an image, this image is not necessarily displayable as a two-dimensional depiction on a display screen. Rather, the image is an array of data that represents the quantitative and qualitative nature of the electromagnetic spectrum (or some portion thereof) received by the camera of the electronic device when it was exposed to the scene.

On its own or working with other devices or computer systems, the electronic device analyzes the image of the scene to detect, determine, and/or identify the type or class of biological cells therein. It may do this, at least in part, by using distinguishing molecules of the cells that are observable using the electromagnetic spectrum. That is, the electronic device captures the observable electromagnetic spectrum (e.g., visible and/or non-visible) that is reflected, scattered, emitting, etc. from the in-situ cells of a captured sane to determine the molecules of those cells.

Some of these molecules are indicative of certain classes, types, or particular cells. Such molecules are called marker biomolecules herein. The electronic device can determine which cell types or class are present in a captured scene by the on the particular ones of, the types of, and the proportions of the biomolecules detected therein.

In addition, the electronic device may include or may have one or more environmental sensors that are designed to measure one or more environmental factors associated with the in situ biological cells or the environment surrounding the in situ biological cells.

The electronic device may have or connect to a report system that is designed to report a detection and/or identification of the one or more cell types or classes in the obtained image and in some implementations, the report system is designed to associate the measured environmental factor(s) with the obtained image and/or with the detected cell.

Correlation Engine

The system 460 includes a correlation engine 462. Based on the image-based data from multiple devices, environmental data from multiple devices, any other associated data, and the results from the report subsystem, the correlation engine 462 finds hidden patterns and ultimately discovers underlying causes of activity (or lack thereof) of biological cells and/or substances. The correlation engine 462 includes one or more AI/ML/DL engines.

Two of the categories of data are supplied to the correlation engine include cellular/molecular observations and environmental observations. One of the categories is based on the cellular and/or molecular measurements/observations of the scene itself. It may be the full conclusion about the detection/identification of the type/class of cells and/or substances found in the scene or something less than the full conclusion.

The other category is any other environmental factor. Of course, there is myriad of choices and mass amount of data available here. Because of this, the tools of the so-called Big Data are employed to address this.

Inference Engine

The system 460 includes an inference engine 464, which may be implemented with AI/ML/DL engines. Based on the image-based data from multiple devices, environmental data from multiple devices, any other associated data, the results from the report subsystem, and the correlations of the correlation engine 462, the inference engine 464 can draw inferences based on the patterns or links detected by the correlation engine. For example, there may be a direct correlation between ambient humidity and the proliferation of a specific type of biological cell. The inference is that humidity directly affects that type of cell's growth.

If the cell is deemed to be bad, then a human may decide to implement a solution to control the humidity more closely to control the growth more closely. Alternatively, with sufficient automation in place, a computer-controlled HVAC system may be directed to lower the humidity of a room to lessen the chances of the growth of that type of cell.

If strong inferences are formed from the analysis of the data, then more accurate predictions can be made. For example, with sufficient information gathered over a large enough area in real time, an epidemic of an infectious disease may be detected, and its spread predicted so early the spread of the epidemic may be halted long-before the epidemic could take hold.

To further the goal of making better inferences and predictions, the tools of the so-called Big Data may be employed. Big Data is an evolving term that describes the tools used to work with a voluminous amount of structured, semi-structured and unstructured data that has the potential to be mined for information.

Big Data works on the principle that the more you know about anything or any situation, the more reliably you can gain new insights and make predictions about what will happen in the future. By comparing more data points, relationships will begin to emerge that were previously hidden, and these relationships will enable us to learn and inform our decisions.

Most commonly this is done through a process which involves building models, based on the data we can collect, and then running simulations, tweaking the value of data points each time and monitoring how it impacts our results. This process is automated—today's advanced analytics technology will run millions of these simulations, tweaking all the possible variables until it finds a pattern—or an insight—that helps solve the problem it is working on.

Increasingly, data is coming to us in an unstructured form, meaning it cannot be easily put into structured tables with rows and columns. Much of this data is in the form of pictures and videos—from satellite images to photographs uploaded to social networking sites—as well as email and instant messenger communications and recorded telephone calls. To make sense of all of this, Big Data projects often use cutting edge analytics involving artificial intelligence and machine learning. By teaching computers to identify what this data represents—through image recognition or natural language processing, for example—they can learn to spot patterns much more quickly and reliably than humans.

A strong trend over the last few years has been a move towards the delivery of Big Data tools and technology through an "as-a-service" platform. Businesses and organizations rent server space, software systems and processing power from third-party cloud service providers. All of the work is carried out on the service provider's systems, and the customer simply pays for whatever was used. This model is making Big Data-driven discovery and transformation accessible to any organization and cuts out the need to spend vast sums on hardware, software, premises and technical staff.

Distributed Ledgers

With the platform, users may upload and share their own data related to biological tests, experiments, etc. Their data becomes part of the Big Data collection of data and may help form better inferences for others.

As part of this service, the data may be stored in a blockchain fashion to ensure that the data is not altered, deleted, or manipulated. A blockchain is a digitized, decentralized, distributed, public ledger of data transactions. Constantly growing as 'completed' blocks (the most recent transactions) are recorded and added to it in chronological order, it allows participants to keep track of data transactions without central recordkeeping. Each node (a computer connected to the network) gets a copy of the blockchain, which is downloaded automatically.

Ratings & Certifications

The system 460 includes a ranking engine 466. With the ranking engine 466, a ratings and certification program may be offered. For example, a business, such as Hope Hospital 410, may contract with a service to visit their facilities and inspect them. Using NANOBOT™ devices and smartphone devices, the service may inspect various locations inside Hope Hospital 410's buildings.

The service may score the results based on the quantity and type of biological cells discovered in their buildings. This score may be the rating or certification for Hope Hospital 410. This rating may be displayed physically and publicly at Hope Hospital 410. In addition, the rating may be posted on digital resources, such as the hospital's website, social networking sites, and the like.

For example, Hope Hospital may get a cleanliness rating based on the frequency of appearance and the severity of pathobiological cells and/or substances found in their facilities. Similar businesses may be ranked based on this rating system. A consumer may choose to visit the "cleanest" hospital based on such rankings.

In addition to or alternatively, the data upon which the rating system is based may be collected via crowdsourcing by have individuals who are physically in the hospital take measurements as they go about their daily tasks. Businesses may be willing to pay a regular fee to be listed with the rating service.

Amelioration & Delivery

The system 460 includes an amelioration subsystem 468 that ameliorates (e.g., fixes) problems discovered by the reporting subsystem and/or the correlation or inference engines. Indeed, the amelioration subsystem 468 may trigger a delivery of the amelioration in response to such problems.

The amelioration subsystem 468 performs amelioration actions. Examples of such actions include (by way of example and not limitation):

- introducing an active material (e.g., sanitizer, ultraviolet light, cleaning fluid/spray) to a physical location of the pathobiological cell and/or substance to neutralize (e.g., clean, reduce, kill, or eliminate) the pathobiological nature of the detected/identified pathobiological cell and/or substance;
- dispatch or request a visit by a robot or human to a physical location of the pathobiological cell and/or substance to neutralize (e.g., clean, reduce, kill, or eliminate) the pathobiological nature of the detected/identified pathobiological cell and/or substance;
- dispatch or request a visit by a robot or human to a physical location of the pathobiological cell and/or substance to document (e.g., photograph and measure) the conditions around the pathobiological cell and/or substance (e.g., a macroscopic photograph of the physical location);
- activate an operation of a proximate electronic device or system that is proximate a physical location of the pathobiological cell and/or substance to neutralize (e.g., clean, reduce, kill, or eliminate) the pathobiological nature of the detected/identified pathobiological cell and/or substance;
- activate an operation of a proximate camera that is proximate a physical location of the pathobiological cell and/or substance to document (e.g., photograph and video) the area around the pathobiological cell and/or substance;
- trigger formulation of a customized therapeutic and ordering delivery of that therapeutic to specific patients, locations, organizations, and/or regions;
- trigger selection of an available therapeutic and ordering delivery of that therapeutic to specific patients, locations, organizations, and/or regions; and/or
- a combination thereof.

In some Instances, the amelioration operation may include mitigation. For example, a recommendation may be made and/or directions given to institute treatment for an allergy if mold is present, increase the frequency of cancer check-ups, reallocate cleaning resources, etc.

Example Processes

Figure 5:
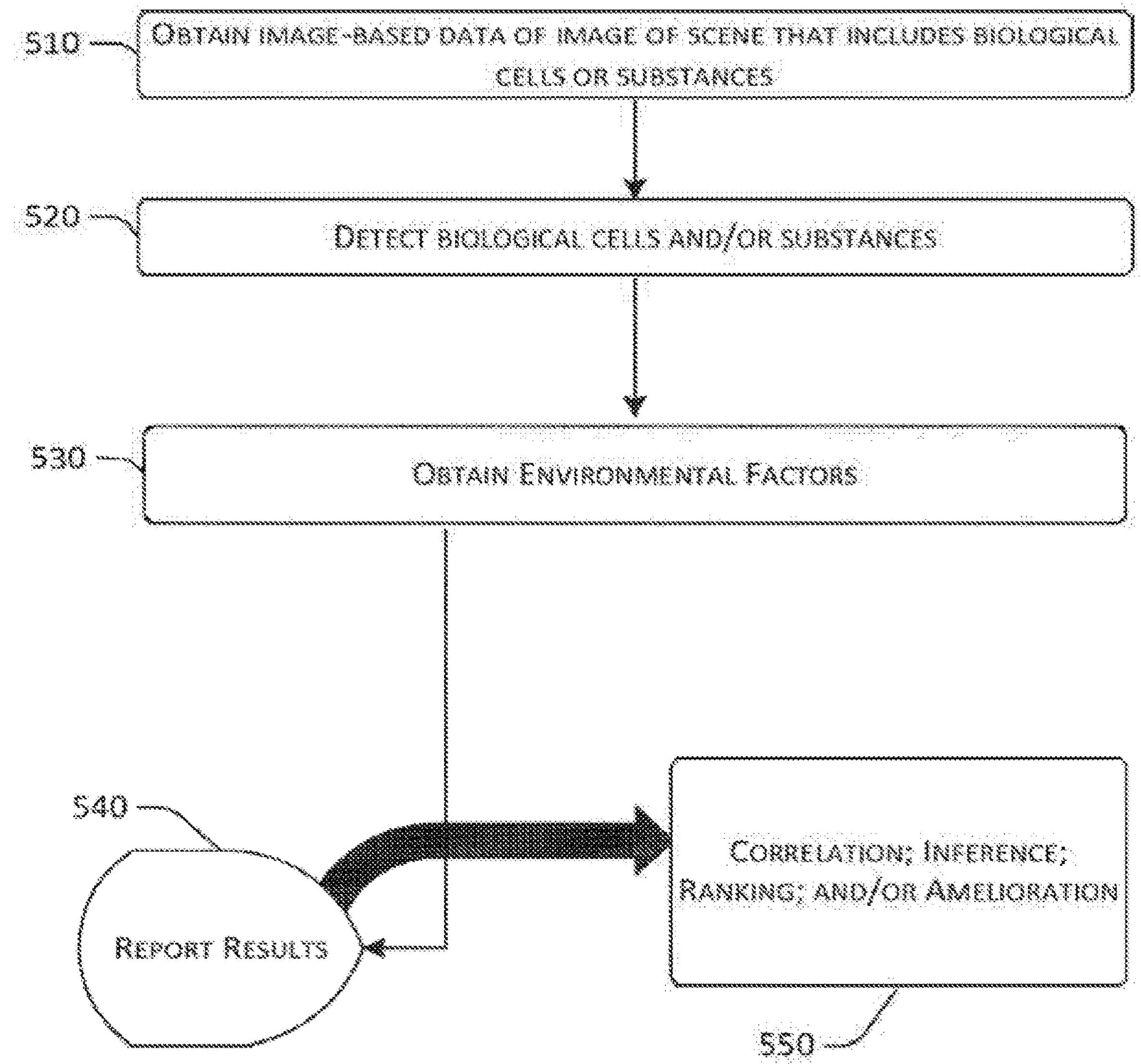
FIG. 5 is a flow chart illustrating an example method in accordance with the present disclosure.

FIG. 5 is a flow diagram illustrating example process 500 that implement the techniques described herein for the data collection and/or analysis for the detection and/or identification of biological cells and/or biological substances. For example, the example process 500 may detect and/or identify pathobiological cells and/or substances.

The example process 500 may be performed, at least in part, by the electronic device 250, by the system-on-a-chip 301, and/or system 440 as described herein. The example process 500 may be implemented by other electronic devices, computers, computer systems, networks, and the like. For illustration purposes, the example process 500 is described herein as being performed by a "system."

At block 510, the system obtains (e.g., via wireless communication) image-based data from one or more of multiple remote monitoring devices. The image-based data from each monitoring device is based on (e.g., derived from) one or more images of a scene proximate to that monitoring device. The proximate scene includes biological cells and/or substances therein. Indeed, the system may obtain image-based data based on a sequence of images of the scene. If any particular type or class of biological cells and/or substances are detected, then the scene included biological cells and/or substances.

A scene may include, for example, one or more surfaces on which the in-scene biological cells and/or substances inhabit; a liquid in which the in-scene biological cells and/or substances inhabit; a bodily fluid in which the in-scene biological cells and/or substances inhabit; an area in which the in-scene biological cells and/or substances inhabit; a volume in which the in-scene biological cells and/or substances inhabit; an area or volume with its dimensions falling below 0.1 mm; or a combination thereof.

In some implementations, the scene includes biologic cells or biologic substances. But, often, the scene includes both. The in-scene biological cells and/or substances may be characterized as: physically located on a surface; physically located in a medium (e.g., blood, bodily fluids, water, air, etc.); undisturbed in their environment; undisturbed and unadulterated; physically located on a surface in a manner that is undisturbed and unadulterated; not relocated for the purpose of image capture; unmanipulated for the purpose of image capture; or on a surface that is unaffected by the scene-capture system.

In some implementations, the biologic cells and/or substances are in situ and in other implementations, they are in the lab.

The obtained image is micrographic, spectrographic, and/or digital. In some implementations, the obtained image is micrographic because the image of the scene is captured at least in part: on a microscopic scale; using microscope like magnification; includes microscopic structures and features; includes structures and features that are not visible to a naked human eye; or a combination thereof.

In some implementations, the obtained image is spectrographic at least in part because the image of the scene is captured using some portion of the electromagnetic spectrum (e.g., visible spectrum of light, infrared, x-rays, gamma rays, ultraviolet) as it interacts with matter, such interactions include, for example, absorption, emission, scattering, reflection, and refraction.

The image may be obtained by capturing a digital image of the scene, and that scene may include in-scene biological cells and/or substances therein. In addition, digital enhancement of a captured digital image may be employed to better reveal the in-scene biological cells and/or substances in the captured image. The obtained image is digital at feast in part because the image of the scene has handled as a set of machine readable data.

At block 520, the system analyzes the image-based data and/or the environmental data. Based on that analysis, the system detects and/or identifies a type or class of biological cells and/or substance amongst the in-scene biological cells and/or substances of each device or amongst several of the devices.

The system may employ an AI/ML/DL engine to perform or assist in the performance of the detection and/or identification of one or more biological cells and/or substances.

The AI/ML/DL engine functionality may be split across the platform. That is, the devices may perform pre-processing of the image using AI/ML/DL engine and send the results as the image-based data to the system 440 for further processing herein. In that case, the device 414 communicates in real time (or nearly so) with the platform. In this way, the intensive processing is offloaded from the devices to the platform.

The biologic detection subsystem 444 analyzes the image-based data of the scene to detect, determine, and/or identify the type or class of biological cells and/or substances therein. It may do this, at least in part, by using distinguishing molecules of the cells that are observable using the electromagnetic spectrum. In some implementations, other data (such as chemical reactions or excitation) may be included in the analysis.

Examples of one or more of the types or classes of biological cells that may be detected and/or identified at block 520 includes (by way of example, but not limitation): cells of a multicell biological organism; cells of a tissue or organ of a multicell biological organism, cells of a tumor or growth multicell biological organism; single-celled organism; microbes; microscopic organisms; single-celled organism; living things that are mo small to be seen with a human's naked eye; a biological creature that can only be seen by a human with mechanical magnification; microscopic spores; a combination thereof. In addition, the biological cells have a size range that is selected from a group consisting of: 10-100 nanometers (nm); 10-80 nm; 10-18 nm; 15-25 nm; and 50-150 nm.

Furthermore, biological cells and/or substances may be typed or classified as pathobiological, not pathobiological, pathobiology unknown, or pathobiology not-yet-known. The pathobiological biological cells and/or substances may be classified or typed as (byway of example and not limitation): pathobiological cells; pathobiological substances; toxic; poisonous; carcinogenic; diseased cells; cancer cells; infectious agents; pathogens; bioagents; disease producing agents; or combination thereof.

Of those biological cells that are characterized as microbes, they may be further typed or classified as one or more of the following (by way of example and not limitation): single-celled organisms; bacteria; archaea; fungi; mold; protists; viruses, microscopic multi-celled organisms; algae, bioagents; spores; germs; prions; a combination thereof.

In some instances, the operation at block 520 may include an identification of one or more particular biologic cells and/or substances in the scene. Rather than just detecting the type or class (e.g., pathogen), the operation may identify the member of that type or class (*Listeria*). Examples of particular members of a class or type that this operation may identify include: *Clostridium botulinum, Streptococcus pneumoniae, Mycobacterium tuberculosis, Escherichia coli* o157:h7, *Staphylococcus aureus, Vibrio cholerae*, ebola, hiv, influenza virus, norovirus, zika virus, *Aspergillus* spp, and *Entamoeba histolytica.*

At block 520, one or more implementations of the detection and/or identification includes operations to:

- access a database of signatures of biological cells and/or substances;
- isolate a biological cell and/or substance in the obtained image;
- correlate the isolated biological cell and/or substance to at least one signature in the database;
- determine that the correlation is significant enough to indicate a sufficient degree of confidence to identify the isolated biological cell and/or substance as being a biological cell and/or substance;
- in response to that correlation determination, label the isolated biological cell and/or substance as being the determined biological cell and/or substance.

An example of a "sufficient degree of confidence" includes more likely than not. A confidence factor for the "sufficient degree of confidence" may be weighted relative to a perceived degree of threat. For example, a pathogen that is unlikely to cause a human infection may have a very high confidence factor (e.g., 80%). Thus, a detection may only be noted if it is at least 80% likely to be that particular pathogen. Conversely, a pathogen may be particularly dangerous (e.g., small pox) and have only a small confidence factor (e.g., 20%). In this way, the dangerous pathogen is detected even it is more likely that the pathogen was misdetected.

Other implementations of the detection and/or identification include operations to:

- provide the obtained image to a trained biological detection/identification (detection and/or identification) engine, the trained biological detection/identification engine being an AI/ML/DL engine trained to detect and/or identify biological cells and/or substances based on a training corpus of signatures of biological cells and/or substances;
- receive a positive indication from the biological detection/identification engine that the obtained image includes a biological cell and/or substance therein and/or the identity of that biological cell and/or substance.

Still other implementations of the detection and/or identification include operations to:

- provide the obtained image to a trained biological detection/identification engine, the trained biological detection/identification engine being an AI/ML/DL engine trained to detect and/or identify pathobiological cells and/or substances based on a training corpus of signatures of pathobiological cells and/or substances;
- receive a positive indication from the biological detection/identification engine that the obtained image includes a pathobiological cell and/or substance therein and/or the identity of that pathobiological cell and/or substance,
- wherein the obtained image includes data captured from the visible and/or non-visible electromagnetic spectrum of the scene.

Other variations of the detection and/or identification operations described above may be focused pathobiological cells and/or substances in particular.

At block 530, from each of the multiple devices, the system gathers one or more environmental factors associated with the in-scene biological cells and/or substances or the environment surrounding the in-scene biological cells and/or substances. The environmental data being based on an environmental factor associated with the in-scene biological cells and/or substances of each device or the environment surrounding the in-scene biological cells and/or substances of each device. In some implementations, the system may acquire information related to or associated with the scene.

The measured environmental factors include (but are not limited to): temperature; timestamp (e.g., time and date, local time, incremental time, etc.), humidity; barometric pressure; ambient sound; location; ambient electromagnetic activity; ambient lighting conditions; WiFi fingerprint; signal fingerprints; GPS location; airborne particle or chemical detector/counter; gases; radiation; air quality; atmospheric pressure; altitude; Geiger counter; proximity detection; magnetic sensor; rain gauge; seismometer; airflow; motion detection; ionisation detection; gravity measurement; photoelectric sensor; pieso capacitive sensor; capacitance sensor; tilt sensor; angular momentum sensor; water-level (i.e., flood) detection; flame detector; smoke detector; force gauge; ambient electromagnetic sources; RFID detection; barcode reading; or a combination thereof.

At block 540, the device reports a detection and/or identification of the type of biological cell and/or substances in the scene proximate to the monitoring device. For example, the device may provide a report or notification via a user interface to a user. A messaging system (e.g., email or SMS) may be used for such notification.

In some implementations, the system may report that the type of biological cell and/or substances in the obtained image is a category flagged for further research and inquiry. For example, the device may be unable to detect the type of cell or substance. In that case, the device flags this as a something worthy of further inquiry. This category may be the default when there is a failure to detect or identify a cell or substance. In some instances, this category is only triggered with particular markers (e.g., chemicals or structures) are detected.

The report or notification may include the following (by way of example and not limitation) operations: send a communication (e.g., message, postal mail, email, text message, SMS message, electronic message, etc.) to a human or machine that is designated to receive such communications via wired or wireless communications mechanisms; send a notification (e.g., message, postal mail, email, text message, SMS message, electronic message, push notices, etc.) to a human or machine that is designated to receive such notification via wired or wireless communications mechanisms; update a database designated to receive such updates via wired or wireless communications mechanisms; store in memory (e.g., local or remote) the detection; or a combination thereof.

In addition, at block 540, the device associates the measured environmental factor and/or the associated factor with the obtained image and/or with the detected type or class of biological cell and/or substance. This association may perform in one more database. Indeed, such a database may take the form of a distributed ledger (DL) technology.

As part of block 550, the report operation may send 449 its results and associated data (image-based data and/or environmental data) to the system 460.

At block 560, the system 460 performs correlation, inference, ranking, and/or amelioration operations in response to the results and associated data (image-based data and/or environmental data) sent 449 to system 460.

Glossary

The following is a list of relevant terms used herein. Unless the context in which the term is used indicates differently, the terms of this glossary may be understood as being described in this glossary in accordance with the technology described herein.

Electronic Device: An apparatus that includes one or more electronic components designed to control or regulate the flow of electrical currents for the purpose of information processing or system control. An electronic device may include some mechanical, optical, and/or otherwise non-electronic parts in addition to its electronic components. Examples of such electronic components include transistors, diodes, capacitors, integrated circuits, and the like. Often such devices have one or more processors that are capable of executing instructions, memories, input/output mechanisms (e.g., display screens, touchscreens, cameras, etc.), and communication systems (e.g., wireless networking and cellular telephony). Examples of an electronic device contemplated herein includes a smartphone, a tablet computer, medical equipment, a microscope, a smartdevice, a computer, a standalone unit, a collection of cooperative units, a button-sited unit, system-on-a-chip, a device on a chip, an accessory to a smartphone or smartdevice, an ambulatory device, a robot, swallowability device, an injectable device, or the like. Depending on the implementation, the electronic device may be characterized as: portable; handheld; fits into a typical pocket; lightweight; portable and with fixed (non-aimable) optics—thus, the device must be moved to aim the optics; with aimable optics—thus, the device need not be moved to aim the optics; or a combination thereof. In addition, an implementation of an electronic device may be characterized as a smartdevice (e.g., smartphone or tablet computer) with its own processor and camera (as its scene-capture system); an accessory or case for a smartdevice that operatively attaches to the smartdevice and adds additionally processing capabilities and functionalities for its scene-capture system; stand-alone device with its own processor and camera (as its scene-capture system); ambulatory device that can move under its own power; a device-on-a-chip; system-on-a-chip; or a wireless device that is configured to interconnect with a wireless network of such devices, this device has its own processor camera (as its scene-capture system).

System: An assemblage or combination of things, parts, or components that form a unitary or cooperative whole. In some instances, a system and platform are used synonymously.

Scene: An area, place, location, scenario, etc. that is in view of the scene capture system.

Image: An array (e.g., two-dimensional) of data derived from and mapped to a scene. An image may be an array of measured data regarding the electromagnetic spectrum emanating from, reflected off, passing through, scattering off of, etc. the contents (e.g., matter) of the scene. The image has an inherent frame or bound around or surrounding the subject scene.

In situ: Describes something that is situated in the original, natural, or existing place or position. Something that is in place or position. It is undisturbed.

In-the-field: A synonym for in situ.

In the lab: Describes the opposite of in situ. That is, it describes something that has been removed from its original or natural place or position. It is something that is not in place. It has been repositioned.

Biological cell: In biology, a cell is the basic structural, functional, and biological unit of all known living organisms. Typically, biological cells consist of cytoplasm enclosed within a membrane, which contains many biomolecules such as proteins and nucleic acids. Organisms can be classified as single celled or unicellular (consisting of a single cell, including bacteria) or multicellular (such as plants and animals). While the multicellular plants and animals are often visible to the unaided human eye, their individual cells are visible only under a microscope, with dimensions between 1 and 100 micrometers.

Biological substance: As used herein, a biological substance is not itself a biological cell. Rather, this is a substance is strongly associated with biological cells or lifeforms. In particular, a biological substance maybe part of or produced by a biological cell or lifeform. In other instances, a biological substance is capable of affecting a lifeform (or some portion thereof).

As used herein, this refers to both "biological cells" and "biological substances."

Type or class of biological cell: The cells may be classified, categorized, or typed based on identifiable characteristics (e.g., physical, chemical, behavioral, etc.). For example, some cells may be classified as pathological because they cause disease. Some may be a diseased typed because they are malfunctioning and/or infected.

Micrographic: An image is classified as micrographic when it captures content that is on a microscopic scale. Such content includes things that are less than 100 micrometers in size. More generally, it includes items smaller than a macroscopic scale (which are visible to the unaided human eye) and quantum scale (i.e., atomic and subatomic particles).

Spectrographic: An image is classified as spectrographic when it captures the interaction between matter and some portion of the electromagnetic spectrum. Examples of such interactions included absorption, emission, scattering, reflection, refraction, translucency, etc.

Optical: Physics that involves the behavior and properties of light, including its interactions with matter and instruments that use or detect it. However, optics involve more than just the visible spectrum.

Visible Spectrum: This is part of the spectrographic image but specifically includes some portion of the visible spectrum (i.e., light) and excludes the non-visible portions.

Digital: This describes data that is formatted and arranged so as to be managed and stored by a machine, computer, digital electronic device, or the like. A data in the form of a digital signal uses discrete steps to transfer information.

Disease: Any disordered or malfunctioning lifeform or some portion thereof. A diseased lifeform is still alive but ill, sick, ailing, or the like.

Pathological: Something that is capable of causing disease or malfunction in a lifeform (or a portion thereof). A pathogen is pathological.

Pathobiological: Something is pathobiological if it is either capable of causing the disease to a lifeform (or some portion thereof) or is a diseased lifeform (or some portion thereof).

Pathobiological cell: A biological cell that is pathobiological.

Pathobiological substance: This is a substance that is either capable of causing the disease to a lifeform (or some portion thereof) or is associated with a diseased lifeform (or some portion thereof). The substance is not itself a biological cell.

Pathobiological cells and/or substances: As used herein, the term "pathobiological" modifies both "cell" and "substance."

Pathogen: A biological cell (e.g., unicellular organism) that is capable of causing a disease. More generally, anything that can cause or produce disease.

Diseased cell: A biological cell (e.g., cancerous cell) that is alive but diseased.

Lifeform: The body form that characterizes an organism. Examples of lifeforms include:

Plants—Multicellular, photosynthetic eukaryotes

Animals—Multicellular, eukaryotic organisms

Fungus—Eukaryotic organisms that include microorganisms such as yeasts and molds Protists—a Eukaryotic organism that is not an animal, plant or fungus Archaea—Single-celled microorganisms Bacteria—Prokaryotic microorganisms Organism: An organism may generally be characterized as containing different levels of the organization; utilizing energy; responding to stimuli/environment; maintaining homeostasis; undergoing metabolism; growing; reproduction; and adapting to its environment.

Environmental factor: It is anything measurable that is capable of affecting the scene or that is associated with the scene. Such things can be abiotic or biotic. Abiotic factors include, for example, ambient temperature, moisture, humidity, radiation, the amount of sunlight, and pH of the water medium (e.g., soil) where a microbe lives. Examples of biotic factors include the availability of food organisms and the presence of conspecifics, competitors, predators, and parasites.

Smartphone: Generally, this term refers to a portable electronic device with features that are useful for mobile communication and computing usage. Such features the ability to place and receive voice/video calls, create and receive text messages, an event calendar, a media player, video games, GPS navigation, digital camera and video camera.

Smartdevice: The concept of a smartdevice includes a smartphone, but it also includes any other portable electronic device that might not have all of the features and functionality of a smartphone. Examples of a smartdevice include a tablet computer, portable digital assistant, smart watches, fitness tracker, location trackers, a so-called internet of-things device, and the like. A smartdevice is an electronic device that is generally connected to other devices or networks via different wireless protocols such as Bluetooth, NFC, Wi-Fi, 3G, etc., that can operate to some extent interactively and autonomously.

Accessory: As used herein, this is an accessory to an electronic device (such as a smartphone or smartdevice). It adds additional functionality and/or capabilities to the electronic device. Examples of such accessories include a smartwatch or electronically enabled phone case.

Other Applications

In addition to the example scenarios and applications discussed above, the following are other example scenarios and applications in which the technology described herein may be employed. Of course, there are still other scenarios and applications in which the technology described herein may be employed, but they are not listed here.

Hospital cleanliness: Using a handheld device, the surfaces and equipment may be regularly checked to confirm their cleanliest and alert for the need to redouble sanitation/cleanliness procedures. Other forms of a device (e.g., robot, mounted device, etc.) may be used for the same purposes.

In-room monitoring: Using one or more of small wireless communicating devices, critical areas may be continuously monitored for any dangers (e.g., pathogens). For example, a fixed device may be placed in the HVAC ducting of a building to monitor the presence of potentially harmful bacteria or allergens in the ventilation system. In another example, an ambulatory device (e.g., robot) may travel around a room looking for potentially infectious agents.

Application of sanitizers and cleaners: A robotic version of the electronic device may be particularly suited for both detecting potentially dangerous pathogens and neutralizing the threat by delivering sanitizing and/or cleaning agents to an area inhabited by the dangerous pathogens.

On-person monitoring: Using a device-on-a chip approach, a person may discretely wear a device designed to monitor the surfaces and liquids that the person encounters each day. Alternatively, the device may be attached to the person herself to monitor her skin or anything on the skin.

In vivo monitoring: A highly miniaturized device may be injected into the bloodstream of an animal or human. The device may passively flow with the blood, or it may have its own propulsion system. This device seeks out diseased cells (e.g., cancer) in the bloodstream or in tissues accessible therefrom.

Application of medicine: A version of the device may be placed on or in a living body to respond to the detection of diseased cells by delivering medicine designed to eliminate that disease.

Additional and Alternative Implementation Notes

With some implementations, the technology is anchored by a platform. Depending on the implementation, a platform may be a system or device that includes just hardware (e.g., semiconductor chips, printed circuit boards, enclosure, etc.) or just firmware or some combination thereof. In other implementations, the platform may include a combination of software with hardware, firmware, or both.

While many implementations of the technology described herein are directed towards actions directed at in situ subjects (e.g., pathobiological cells and substances), some implementations may involve "in the lab" conditions. That is, the subject of the actions of these implementations are not necessarily in situ or undisturbed. Indeed, the subject may be repositioned, relocated, adjusted, adulterated, etc. The subject of these implementations may be handled in the traditional manner, such as microbes may be cultured in a petri dish. In this case, these implementations may be incorporated into or be an accessory to traditional data gathering equipment, such as a microscope.

In the above description of example implementations, for purposes of explanation, specific numbers, materials configurations, and other details are set forth in order to better explain the present disclosure. However, it will be apparent to one skilled in the art that the subject matter of the claims may be practiced using different details than the examples ones described herein. In other instances, well-known features are omitted or simplified to clarify the description of the example implementations.

The terms "techniques" or "technologies" may refer to one or more devices, apparatuses, systems, methods, articles of manufacture, and/or executable instructions as indicated by the context described herein.

As used in this application, the term "or" is intended to mean an inclusive "or" rather than an exclusive "or." That is, unless specified otherwise or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more," unless specified otherwise or clear from context to be directed to a singular form.

These processes are illustrated as a collection of blocks in a logical flow graph, which represents a sequence of operations that may be implemented in mechanics alone, with hardware, and/or with hardware in combination with firmware or software. In the context of software/firmware, the blocks represent instructions stored on one or more non-transitory computer-readable storage media that, when executed by one or more processors or controllers, perform the recited operations.

Note that the order in which the processes are described is not intended to be construed as a limitation, and any number of the described process blocks can be combined in any order to implement the processes or an alternate process. Additionally, individual blocks may be deleted from the processes without departing from the spirit and scope of the subject matter described herein.

The term "computer-readable media" is non-transitory computer-storage media or non-transitory computer-readable storage media. For example, computer-storage media or computer-readable storage media may include, but are not limited to, magnetic storage devices (e.g., hard disk, floppy disk, and magnetic strips), optical disks (e.g., compact disk (CD) and digital versatile disk (DVD)), smart cards, flash memory devices (e.g., thumb drive, stick, key drive, and SD cards), and volatile and non-volatile memory (e.g., random access memory (RAM), read-only memory (ROM)).

What is claimed is:

1. A system comprising:

a data communication subsystem to obtain image-based data from a remote monitoring device, the image-based data from monitoring device being derived from one or more images of a scene proximate to the monitoring device and the proximate scene including biological cells or substances therein, wherein the data communication system obtains environmental data based on an environmental factor associated with the in-scene biological cells or substances or the environment surrounding the in-scene biological cells or substances;

a biologic detection subsystem to analyze the image-based data and detect a type or class of biological cells or substance amongst the in-scene biological cells or substances;

a report subsystem to report detection of the type of biological cells or substances in the scene proximate to the monitoring device;

wherein the environmental factors are selected from a group consisting of:

temperature;
timestamp;
humidity;
barometric pressure;
ambient sound;
location;
ambient electromagnetic activity;
ambient lighting conditions;
WiFi fingerprint;
GPS location;
airborne particle counter;
chemical detection;
gases;
radiation;
air quality;
airborne particulate matter;
atmospheric pressure;
altitude;
Geiger counter;
proximity detection;
magnetic sensor;
rain gauge;
seismometer;
airflow;
motion detection;
ionization detection;
gravity measurement;
photoelectric sensor;
piezo capacitive sensor;
capacitance sensor;
tilt sensor;
angular momentum sensor;
water-level detection;
flame detector;
smoke detector;
force gauge;
ambient electromagnetic sources;
RFID detection;
barcode reading; and
a combination thereof.

2. A system of claim 1, wherein the image-based data includes a selected portion of a single image of the scene proximate to the monitoring device.

3. A system of claim 1, wherein the image-based data includes selected portions of each of multiple images of the images of the scene proximate to the monitoring device.

4. A system of claim 1, wherein the type or class of detected biological cell or substance is a pathobiological cell or substance.

5. A system of claim 4, wherein the pathobiological cells include:

pathologic cells;
diseased cells;
cancer cells;
infectious agents;
pathogens;
bioagents;
disease-producing agents; or
a combination thereof.

6. A system of claim 1, wherein the in-scene biological cells or substances are in situ.

7. A system of claim 1, wherein the one or more images of the scene proximate to the monitoring device is micrographic, spectrographic, or digital.

8. A system of claim 1, wherein the in-scene biological cells or substances include biological cells or substances that are characterized as:

physically located on a surface;
physically located in a medium;
undisturbed in their environment;
undisturbed and unadulterated;
physically located on a surface in a manner that is undisturbed and unadulterated;
not relocated for the purpose of image capture;
unmanipulated for the purpose of image capture; or
on a surface that is unaffected by the monitoring device.

9. A system of claim 1, wherein the biological cells are characterized as:

cells of a multicell biological organism;
cells of a tissue or organ of a multicell biological organism;
cells of a tumor or growth multicell biological organism;
single-celled organism;
microbes;
microscopic organisms;
single-celled organism;
living things that are too small to be seen with a human's naked eye;
a biological creature that can only be seen by a human with mechanical magnification;
microscopic spores; or
a combination thereof.

10. A system of claim 1, wherein the biological cells are characterized as microbes that are characterized as:

single-celled organisms;
bacteria;
archaea;
fungi;
mold;
protists;
viruses;
microscopic multi-celled organisms;
algae;
bioagents;
spores;
germs;
prions; or
a combination thereof.

11. A system of claim 1, wherein the image-based data is derived from a sequence of images of the scene.

12. A system of claim 1, wherein the environmental factors on which the environmental data is based includes biotic, abiotic, and associated factors.

13. A system of claim 1, wherein the report subsystem to associate the obtained environmental data with the image-based data and/or with the detected type or class of biological cell or substance.

14. A system of claim 1, wherein the detection includes operations to:

access a database of signatures of biological cells or substances;

isolate a biological cell or substance using the image-based data of the scene proximate to the monitoring device;

correlate the isolated biological cell or substance to at least one signature in the database;

determine that the correlation identifies the isolated biological cell or substance as being a biological cell or substance;

in response to that correlation determination, label the isolated biological cell or substance as being the determined biological cell or substance.

15. A system of claim 1, wherein the detection includes operations to:

provide the image-based data of the scene proximate to the monitoring device to a trained biological detection engine, the trained biological detection engine being an artificial intelligence/machine learning/deep learning (AI/ML/DL) engine trained to detect or identify biological cells or substances based on a training corpus of signatures of biological cells or substances;

receive a positive indication from the biological detection engine that the scene proximate to the monitoring device includes a biological cell or substance therein or identity of that biological cell or substance.

16. A system of claim 1, wherein the detection includes operations to:

provide the image-based data of the scene proximate to the monitoring device to a trained biological detection engine, the trained biological detection engine being an artificial intelligence/machine learning/deep learning (AI/ML/DL) engine trained to detect or identify biological cells or substances based on a training corpus of signatures of biological cells or substances;

receive a positive indication from the biological detection engine that the scene proximate to the monitoring device includes a biological cell or substance therein or identity of that biological cell or substance, wherein the image-based data of the scene proximate to the monitoring device includes data captured from the visible or non-visible electromagnetic spectrum of the scene.

17. A system of claim 1, wherein the report system to report an identification of the biological cell or substance of the scene proximate to the monitoring device.

18. A system of claim 1, wherein the report of the report system is characterized by performing operations that:

send a communication to a human or machine that is designated to receive such communications via wired or wireless communications mechanisms;

send a notification to a human or machine that is designated to receive such notification via wired or wireless communications mechanisms;

update a database designated to receive such updates via wired or wireless communications mechanisms;

store the detection in a memory; or a combination thereof.

* * * * *